United States Patent [19]

Wani et al.

[11] Patent Number: 5,053,512

[45] Date of Patent: * Oct. 1, 1991

[54] TOTAL SYNTHESIS OF 20(S) AND 20(R)-CAMPTOTHECIN AND COMPTHOTHECIN DERIVATIVES

[75] Inventors: Mansukh C. Wani, Durham; Allan W. Nicholas, Raleigh; Monroe E. Wall, Chapel Hill, both of N.C.

[73] Assignee: Research Triangle Institute, Research Triangle Park, N.C.

[*] Notice: The portion of the term of this patent subsequent to Jan. 16, 2007 has been disclaimed.

[21] Appl. No.: 511,953

[22] Filed: Apr. 17, 1990

Related U.S. Application Data

[63] Continuation of Ser. No. 38,157, Apr. 14, 1987, abandoned.

[51] Int. Cl.$^5$ .............. C07D 491/147; C07D 491/22; A61K 31/47
[52] U.S. Cl. ........................................ 546/41; 546/48; 546/92
[58] Field of Search ..................... 546/48, 41

[56] References Cited

U.S. PATENT DOCUMENTS

| | | | |
|---|---|---|---|
| 4,031,098 | 6/1977 | Sugasawa | 546/48 |
| 4,473,692 | 9/1984 | Miyasaka et al. | 546/48 |
| 4,545,880 | 10/1985 | Miyasaka et al. | 204/158 R |
| 4,604,463 | 8/1986 | Miyasaka et al. | 544/125 |
| 4,778,891 | 10/1988 | Tagawa et al. | 546/18 |
| 4,894,456 | 1/1990 | Wall et al. | 546/41 |
| 4,914,205 | 4/1990 | Sawada et al. | 546/70 |
| 4,943,579 | 7/1990 | Vishnuvajjala et al. | 514/283 |
| 4,981,968 | 1/1991 | Wall et al. | 544/361 |

FOREIGN PATENT DOCUMENTS

| | | |
|---|---|---|
| 0074256 | 3/1983 | European Pat. Off. |
| 0220601 | 5/1987 | European Pat. Off. |
| 321122 | 6/1989 | European Pat. Off. |
| 59-05188 | 1/1984 | Japan |
| 0005188 | 1/1984 | Japan .......... 546/48 |
| 59-51287 | 3/1984 | Japan |
| 59-51289 | 3/1984 | Japan |
| 61-85319 | 4/1986 | Japan |
| 61-85389 | 4/1986 | Japan |
| 1085389 | 4/1986 | Japan .......... 546/48 |
| 61-50985 | 8/1986 | Japan |

OTHER PUBLICATIONS

*Cancer Research*, (1989) vol. 49, 4385–5489, "DNA Topoisomerase I–Meditated DNA Cleavage and Cytotixicity of Camptothecin Analogues", Hisang et al.

*Cancer Research*, (1989), vol. 49, 1465–1469, "Structure-Activity Study of the Actions of Camptothecin Derivatives on Mammalian Topoisomerase I . . ." Jaxel et al.

*The Journal of Biological Chemistry*, (1985, 260, 14873–14878, "Camptothecin Induces Protein-Linked DNA Breaks Via Mammalian DNA Topoisomerase I" Hsiang et al.

*J. Med. Chem.*, (1980), 23, 544–560, "Plant Antitumor Agents. 18.[1] Synthesis and Bilogical Activity of Camptothecin Analogues", Wani et al.

*J. Med. Chem.*, (1986), 29, 1553–1555, "Plant Antitumor Agents 22.[1] Isolation of 11-Hydroxycamptothecin from Camptotheca Acuminata Decne . . ." Wall et al.

*Journal of Labelled Compounds and Radiopharmaceuticals*, (1981), 18, 319–329, "The Preparation of Tritium and Deuterium-Labelled Camptothecin", Ronman et al.

*J. Medicinal Chemistry*, (1987), 30, 1774–1779, "Plant Antitumor Agents 25.[1] Total Synthesis and Antileukemic Activity of Ring A . . ." Wani et al.

*J. Medicinal Chemistry*, (1990), 33, 972–978, "Plant Antitumor Agents. 29.[1] Synthesis and Biological Activity of Ring D and Ring 3 . . ." Nicholas et al.

(List continued on next page.)

Primary Examiner—Diana Rivers
Attorney, Agent, or Firm—Oblon, Spivak, McClelland, Maier & Neustadt

[57] ABSTRACT

The invention relates to a method of producing 20(S)-comptothecin, 20(R)-camptothecin and analogs thereof. The method involves the resolution of an mixture of enantiomers of an intermediate lactone.

12 Claims, 2 Drawing Sheets

OTHER PUBLICATIONS

J. Org. Chem. (1974), 39, 303–311, "Synthesis of Some De and CDE Ring Analogs of Camptothecin", Plattner et al.

J. of Am. Chem. Soc. (1972), 94, 8615, "Synthesis of Some De and CDE Ring Analogs of Camptothecin" Plattner et al.

*J. Org. Chem.*, (1974), 39, 3430–3432, "Synthesis of Biological Evaluation of De-AB-Camptothecin", Danishefsky et al.

Govindachari et al., 453–454, "9-Methoxycamptothecin. A New Alkaloid from Mappia Foetida Miers".

*Chem. Ber.*, (1978), 111, 3403–3411, "Total Synthesis of 7-Methoxycamptothecin", Baxmann et al.

*Proc Annu. Meet. Am. Assoc. Cancer Res,* (1988), 29, A1080, "Structure-Activity Study of the Relation Between Topoisomerase I Inhibition and Antitumor"... Abstract.

*Proc. Annu. Meet. Am. Assoc. Cancer Res.* (1989), 8, A1019, "A Clinical Study of a Camptothecin Derivative, CPT-11 on Hematological Malignancies", (MTG Abstract).

*J. Med. Chem.*, (1989), 32, 715–720, "Modification of the Hydroxy Lactone Ring of Camptothecin: Inhibition of Mammalian Topoisomerase I and ...", Mong et al. Abstract.

*Science,* (1989), 246, 1046–1048, "DNA Topoisomerase I-Targeted Chemotherapy of Human Colon Cancer in Xenografts", Giovanella et al.

*Proc. Annu. Meet. Am. Assoc. Cancer Res.* (1989), A2476, "Structure-Activity Studies of 20(S)-Captothecin Analogs" (Meeting Abstract).

Baxmann et al., Chem Berichte, vol. 111, pp. 3403–3411 (1978).

Yang et al., Chemical Abstracts, vol. 100: 13943w (1984).

Yakult Honsha Co., Chemical Abstracts, vol. 101: 130670r (1984), Abstract of Japan Kokai 59 46,284.

Hsu et al., Chemical Abstracts, vol. 90: 28930k (1979).

Yang et al., Chemical Abstracts, vol. 100: 139434w (1984).

Tien et al., Chemical Abstracts, vol. 92: 37766e (1980).

Gunasekera et al., Chemical Abstracts, vol. 92: 18799b (1980).

Chen et al., Chemical Abstracts, vol. 94: 90169e (1981).

Kametani et al., Chemical Abstracts, vol. 94: 4143n (1981).

Cai et al., Chemical Abstracts, vol. 95: 133209h (1981).

Miyasaka et al., Chemical Abstracts, vol. 96: 69271p (1982).

Yakult Honsha Co., Chemical Abstracts, vol. 97: 188278b (1982) Abstract of Japan Kokai 82 116,015.

Luo et al., Chemical Abstracts, vol. 101: 78770z (1984).

Nagata et al., Chemical Abstracts, vol. 100: 167724j (1984).

Fukada et al., Chemical Abstracts, vol. 103: 64374c (1985).

Wani et al., J. Med. Chem. 23(5), pp. 554–560 (1980).

Wani et al., J. Med. Chem. 29(11), pp. 2358–2363 (11/86).

Govindachari et al., Ind. J. Chem. 10(4), pp. 453–454 (1972).

Pan et al., Chemical Abstracts, vol. 84: 115629p (1976).

3a, 5' (R), X=O
b, 5' (S), X=O
5a, 5' (R), X=OCH$_2$CH$_2$O
b, 5' (S), X=OCH$_2$CH$_2$O

4a; RR    c, SS
b, SR    d, RS

MOTHER LIQUOR (4b) FROM FIG.1
 1) CONCENTRATE
 2) HOAc
↓
5b
 S-α-METHYLBENZYLAMINE
↓
4c + 4d
 TOLUENE
↓
MOTHER LIQUOR ← 4c (PRECIPITATE)
 HOAc
↓
5b
 H₂SO₄
↓
3b
 O-AMINOBENZALDEHYDE
↓
20(R)-CAMPTOTHECIN 3a, 5' (R), X=O
b, 5' (S), X=O
5a, 5' (R), X=OCH₂CH₂O
b, 5' (S), X=OCH₂CH₂O

4a, RR    c, SS
b, SR     d, RS

TOTAL SYNTHESIS OF 20(S) AND 20(R)-CAMPTOTHECIN AND COMPTHOTHECIN DERIVATIVES

This application is a continuation of application Ser. No. 038,157 filed on Apr. 14, 1987 now abandoned.

BACKGROUND OF THE INVENTION

1. Field of the Invention

The invention relates to a method of resolving mixtures of camptothecin enantiomers and analogs thereof.

2. Discussion of the Background

Camptothecin is a pentacyclic alkaloid initially isolated from the wood and bark of Camptotheca acuminata by Wall et al. (M. E. Wall, M. C. Wani, C. E. Cook, K. H. Palmer, A. T. McPhail, and G. A. Sim, *J. Am. Chem. Soc.*, 94, 388 (1966).

Camptothecin is highly biologically active and displays strong inhibitory activity toward the bio-synthesis of nucleic acids. Additionally, camptothecin exhibits potent anti-tumor activity against experimentally transplanted carcinoma such as leukemia L-1210 in mice or Walker 256 tumor in rats.

Several methods for the synthesis of camptothecin and camptothecin analogs are known. These synthetic methods include (i) methods in which naturally occurring camptothecin is synthetically modified and (ii) totally synthetic methods.

Naturally occurring camptothecin belongs to the 20(S) series of compounds, i.e., the single chiral center in the molecule is in the S-configuration.

Since naturally occurring camptothecin has the S-configuration, synthetic methods which modify naturally occurring camptothecin and which do not affect the naturally-occuring chiral center will produce camptothecin analogs having the S-configuration as well.

There are no known syntheses of pure 20(R)-camptothecin, and analogs thereof. Moreover, most synthetic camptothecin analogs are racemic, i.e., 20RS, and the corresponding pure 20S-analogs are unknown. It is well known that the biological activity of the S and R forms of drugs which are racemates may differ, sometimes one will be active and the other also active, but of a different nature. Alternatively, one of the racemate forms may be active, and the other inactive or more toxic. Hence, the present application which presents for the first time a practical method for the synthesis of pure 20(S)- and 20(R)-camptothecin and analogs thereof will be of great value.

Known synthetic methods for producing camptothecin and camptothecin analogs produce a mixture of 20(R) and 20(S)-camptothecins. In most syntheses a racemic mixture or racemic modification, i.e., a 50/50 mixture of the R and S enantiomers, is produced. Examples of a variety of synthetic routes to camptothecin and camptothecin analogs can be found in the following references: *Sci. Sin. (Engl. Ed)*, 21(1), 87-98 (1978); *Fitoterpapia*, 45(3), 87-101 (1974); *Yakugaku Zashi*, 92(6), 743-6 (1972); *J. Org. Chem.*, 40(14), 2140-1 (1975); *Hua Hsueh Hsueh Pao*, 39(2), 171-8 (1981); *J. Chem. Soc., Perkin Trans* 1, (5), 1563-8 (1981); *Heterocycles*, 14(7), 951-3 (1980); *J. Amer. Chem. Soc.*, 94(10), 3631-2 (1972); *J. Chem. Soc. D*, (7), 404 (1970), *J. Med. Chem.*, 23, 554 (1980) and U.S. Pat. No. 4,031,098. Reviews of synthetic methods can be found in *The Alkaloids*, Brossi, A., Ed. Academic Press, New York (1983) Vol. XXi, Chapt. 4 and *Chem. Heterocycle Compd.*, 25 753 (1983).

A synthetic method of limited practical utility for preparing 20(S)-camptothecin is disclosed in E. J. Corey, D. E. Crouse, J. E. Anderson, *J. Org. Chem.*, 40, 2140 (1975).

The usefulness of a racemic mixture of camptothecin enantiomers, commonly designated as 20(R,S)-camptothecin is limited in view of the fact that the activity of the 20(R) component is largely unknown; present data indicates it is less active as a cytotoxic or antitumor agent and has unknown toxicity. Thus, it would be advantageous to be able to produce the pure enantiomeric compounds separately. A pharmaceutical or veterinary composition comprising only the naturally occurring enantiomer is clearly preferable since the (R)-enantiomer is thought to be inactive or may have undisclosed adverse biological activity. Additionally, required dosages can be reduced since the undesired (R)-enantiomer is no longer present.

A need exists for a method of producing the (R)-enantiomer in a pure state so that its biological activity can be evaluated and tested. Sufficient quantities of the pure enantiomer are also required for any future treatment regimens involving the (R)-enantiomer.

A need exists, therefore, for a method of producing the enantiomers of camptothecin and camptothecin analogs separately and in a pure form.

SUMMARY OF THE INVENTION

Accordingly, one object of the present invention is to provide a method of producing 20(R)-camptothecin and 20(S)-camptothecin separately.

Another object of the present invention is to provide a high yield method of producing substantially pure enantiomers of camptothecin and camptothecin analogs which is simple to perform and has practical utility.

These and other objects of the present invention which will become apparent from the following detailed description have been achieved by a method for producing 20(S)-camptothecin and 20(R)-camptothecin, which involves the steps of (a) reacting a mixture of enantiomeric lactones having formula (I), wherein X is an achiral ketal group which upon treatment with an acid is converted to a keto group,

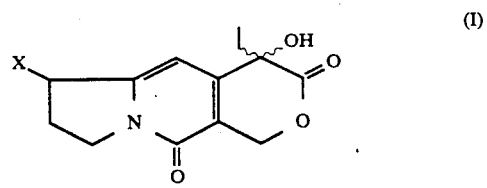

with a substantially enantiomerically pure primary or secondary amine having the formula RR¹NH, wherein R is an alkyl or aralkyl group containing a single chiral carbon and R¹ is hydrogen or an achiral alkyl, aralkyl or aryl group to produce a mixture of diastereomeric amides with formula (II);

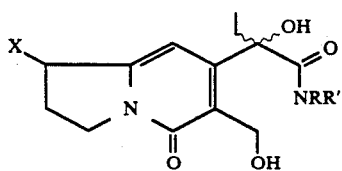

(II)

(b) triturating the diastereomeric amide mixture with a non-polar organic solvent, to produce a precipitate enriched in the more polar amide of the diastereomeric mixture and a mother liquor enriched in the less polar amide of the diastereomeric amide mixture;

(c) separating the precipitate from the mother liquor;

(d) treating the precipitated amide with an acid, whereby the precipitated amide is lactonized and deprotected to give a substantially enantiomerically pure ketolactone having the formula (III); and

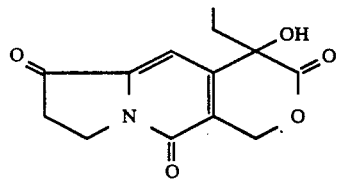

(III)

(e) reacting the ketolactone with an ortho-amino carbonyl compound having the formula

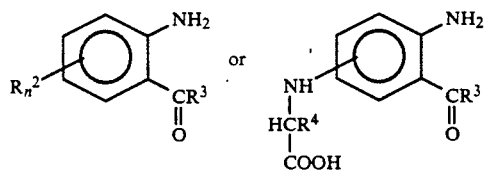

wherein $n=1$ or 2; $R^2$ is a member selected from the group consisting of cyano, methylenedioxy, formyl, hydroxy, $C_{1-8}$ alkoxy, nitro, amino, amido, chloro, bromo, iodo, fluoro, $C_{1-8}$ alkyl, trifluoromethyl, aminomethyl, azido, and hydrazino groups; $R^3$ is H or $C_{1-8}$ alkyl; and $R^4$ is a side-chain of one of the twenty naturally occurring amino acids, and (f) isolating the camptothocein or camptothecin analog.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
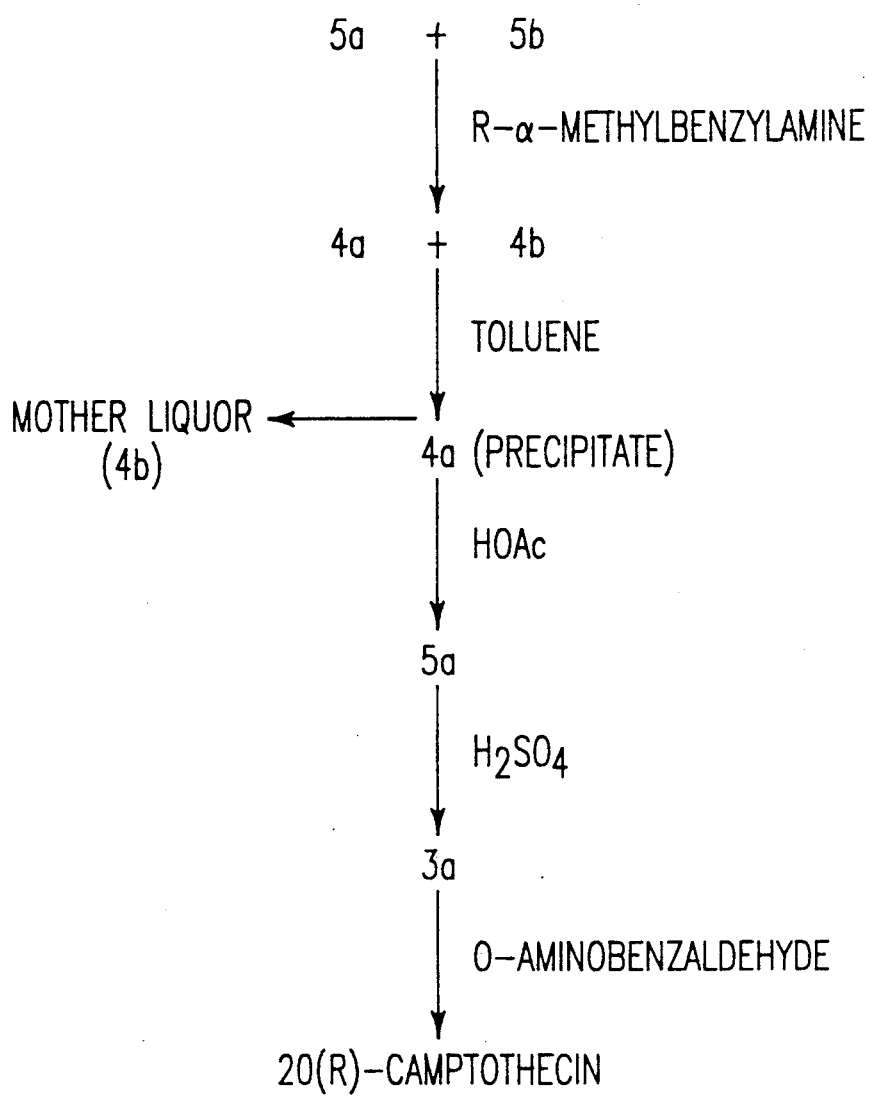
FIG. 1 illustrates the sequence of reactions for producing 20(R)-camptothecin by precipitation of the more polar diastereomeric amide.
Figure 1:
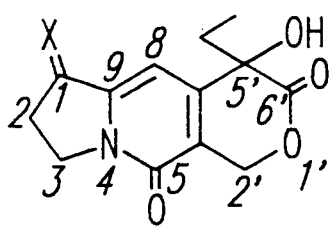
Figure 1:
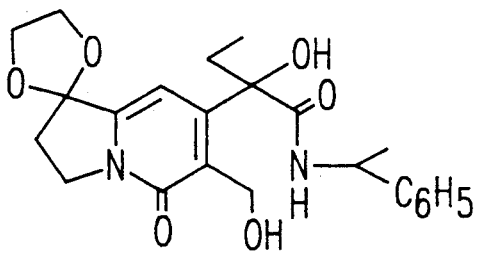
Figure 2:
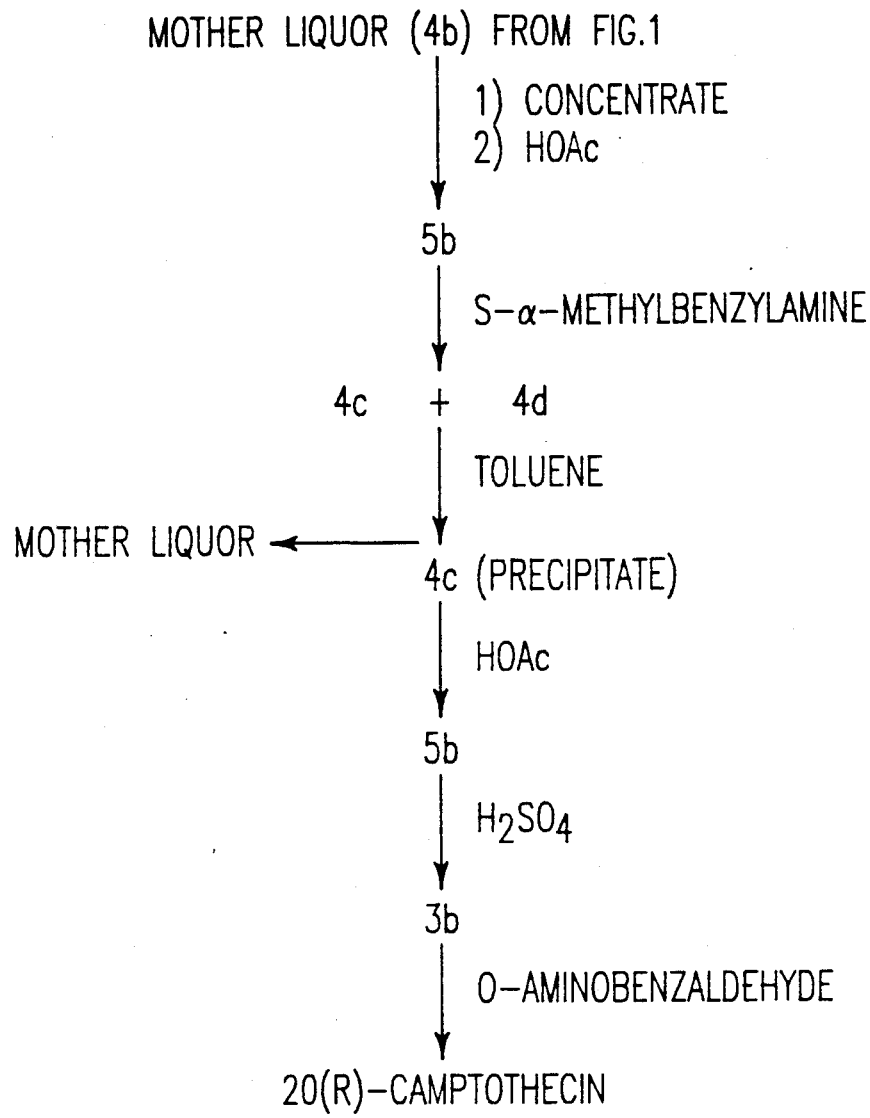
FIG. 2 illustrates the sequence of reactions for producing 20(S)-camptothecin utilizing the recovered less polar diastereomeric amide.
Figure 2:
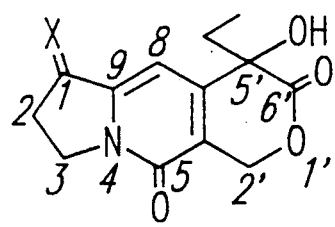
Figure 2:
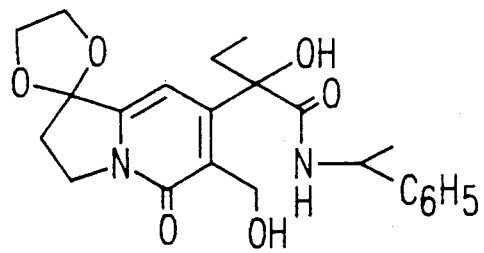

The present synthetic method for the preparation of optically pure 20(R)-camptothecin and 20(S)-camptothecin an  analogs within each series involves the synthesis of a mixture of enantiomers of a tricyclic lactone having formula (I).

This mixture is then resolved by reaction with a suitable optically active amine to yield a mixture of diastereomeric amides having the general structure (II).

By treating the diastereomeric amide mixture with a non-polar organic solvent, a precipitate forms which is enriched in the more polar amide of the diastereomeric mixture. The remaining mother liquor comprising the non-polar organic solvent is therefore enriched in the less polar amide of the diastereomeric mixture. After separating the precipitate from the mother liquor, the precipitate can be treated with an acid whereby the more polar amide is a lactonized and deprotected to give a substantially enantiomerically pure ketolactone having the formula (III) and having the same configuration as the more polar amide of the diastereomeric mixture.

This ketolactone can then be reacted with an appropriate optionally substituted ortho-amino aldehyde or ketone to give camptothecin and camptothecin analogs having the same configuration as the more polar amide of the original diastereomeric mixture.

More specifically, if a racemic (RS) mixture of the tricyclic intermediate I is treated with an optically active amine such as R-(+)-α-methylbenzylamine, a mixture of diastereomeric amides having formula (II) is produced. The diastereomeric amides can be designated as the (R,R)-amide and the (S,R)-amide, respectively. Trituration of this diastereomeric amide mixture with a non-polar organic solvent such as toluene, for example, results in the precipitation of the more polar amide of the diastereomeric pair noted above, i.e. the (R,R)-amide. The mother liquor is therefore enriched in the (S,R)-amide.

After isolating the precipitated (R,R)-amide, it is then treated with acid whereby the more polar (R,R)-amide is lactonized and deprotected to give the (R)-ketolactone having formula (III). The (R)-ketolactone is then reacted with an ortho-aminobenzaldehyde or an ortho-amino aralkyl ketone, i.e., a phenone, in the presence of an acid or base to yield a 20(R)-camptothecin derivative. Preferred phenones have 1-8 carbon atoms in the alkyl group. Particularly preferred ortho-amino compounds are the ortho-aminobenzaldehydes, ortho-aminoacetophenones, and the ortho-aminopropiophenones.

This same sequence of reactions could of course be performed using an optically active (S)-amine, such as S-(−)-α-methylbenzylamine, in which case the diastereomeric mixture would be comprise the (S,S)-amide and the (R,S)-amide and would eventually yield a 20(S)-camptothecin derivative.

Optically active amines which are suitable for use in the invention include any $C_2$-$C_{20}$ optically active primary and secondary amine having a single chiral center and which gives rise to a diastereomeric pair of amides having sufficiently different polarities such that treatment with a non-polar organic solvent results in precipitation of the more polar amide. The optically active amines should be substantially enantiomerically pure. By "substantially enantiomerically pure" is meant an optically active amine which is greater than about 98% pure. To determine whether an amine is suitable for use in the present invention, diastereomeric amides are produced and their ability to be separated by trituration with an organic solvent is evaluated experimentally.

Preferred examples of optically active amines within the scope of the invention are the R and S enantiomers of α-methylbenzylamine, α-(1-naphthyl)-ethylamine, α-(2-naphthyl)ethylamine and amphetamine. Especially preferred amines are the R and S enantiomers of α-methylbenzylamine.

The diastereomeric amide mixture may be treated with any non-polar organic solvent so long as both diastereomeric amides are not equally soluble in the solvent. Suitable solvents include aromatic and aralkyl hydrocarbons as well as straight chain and branched alkyl hydrocarbons having at least five carbon atoms and not more than twenty carbon atoms. Preferred examples are benzene, toluene, xylene, naphthalene, pentane, hexane, cyclohexane, heptane, octane, nonane, and decane. More preferred solvents are the aromatic hydrocarbons with toluene being most preferred.

The precipitate resulting from the trituration of the diastereomeric amide mixture with the non-polar organic solvent is enriched in the more polar amide while the mother liquor is enriched in the less polar amide. By "enriched" is meant that one diastereomer is predominantly present in amounts of about 75–100% relative to the other diastereomer. The relative amounts of each diastereomer can be evaluated by standard analytical techniques such as, for example, high pressure liquid chromatography or thin layer chromatography. The precipitate in the mother liquor can be separated by filtration, decantation, or any other suitable means of separating a precipitate from a liquid.

The precipitate which is enriched in the more polar amide is then treated with acid to regenerate the lactone and also to remove the keto protecting group. The precipitate is enantiomerically enriched in the ketolactone corresponding to the more polar amide. By "enantiomerically enriched" is meant a precipitate having from about 75–100% of one enantiomer. Suitable acids include mineral acids such as HCl, $H_2SO_4$, $HNO_3$ and $H_3PO_4$ and organic acids such as acetic acid and aromatic sulfonic acids, i.e., p-toluenesulfonic acid, with sulfuric acid being preferred. This reaction is carried out in the presence of any suitable solvent such as, for example, tetrahydrofuran, dioxane and dimethoxyethane with dimethoxyethane being preferred.

The lactonization and deprotection steps can be carried out separately if desired. For example, the precipitated amide may be treated with glacial acetic acid to produce the corresponding lactone while leaving the protecting group intact. The lactone can then be treated with an aqueous solution of a mineral acid to remove the keto protecting group. The resulting ketolactone having formula (III) has the same configuration as the more polar diastereomeric amide.

If desired, ketolactone (III) can be obtained in nearly 100% (e.g. >95%) optical purity by an appropriate purification process. A particularly preferred process is recrystallization by dissolving the precipitated diastereomeric amide in a minimum amount of methylene chloride and subsequently diluting with toluene. Other preferred solvents pairs include methylene chloride-benzene, chloroform-toluene and chloroform-benzene. The most preferred solvent pair is methylene chloride-toluene.

Suitable keto protecting groups which may be present in lactone (I) include any group which is acid labile, i.e., may be removed by treatment with acid. The carbonyl of the lactone may be "deprotected" by treatment with acid. Such protecting groups include ketals, thioketals, etc. Suitable protecting groups will not be chiral or contain a chiral atom, since the presence of additional chirality will increase the number of diasteriomers which are possible, which is undesirable. Preferred protecting groups are the $-OCH_2CH_2O-$, $(OMe)_2$ and $-OCH_2C(Me)_2CH_2O-$ groups. A particularly preferred protecting group is the $-OCH_2CH_2O-$ group.

Finally, the ketolactone (III) is reacted with an ortho-aminobenzaldehyde or ortho-amino phenone, preferably an acetophenone or propiophenone in the presence of an acid or base catalyst to yield a camptothecin. If a substituted ortho-aminobenzaldehyde is used, camptothecin analogs can be produced as well. The use of ortho-amino acetophenones and ortho-aminopropiophenones results in the preparation of camptothecin and camptothecin analogs bearing a methyl or ethyl group on $C_7$. Ortho-amino compounds having the formulas shown below are preferred,

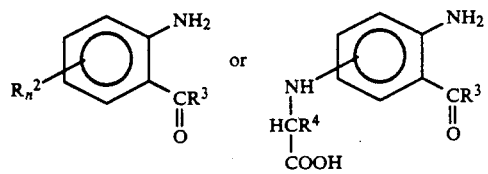

wherein n=1 or 2 and $R^2$ is a member selected from the group consisting of $C_{1-8}$ alkyl, $C_{1-8}$ alkoxy, cyano, methylenedioxy, formyl, hydroxy, nitro, amino, amido, chloro, bromo, iodo, fluoro, aminomethyl, trifluoromethyl, azido, and hydrazino groups, and $R^3$ is a side-chain of one of the twenty naturally occurring amino acids. In this manner, a wide variety of camptothecin analogs can be prepared in optically active form.

This final reaction with an o-aminobenzaldehyde or ortho-amino phenone is known as a Friedlander condensation reaction and may be performed under acidic or basic conditions.

Suitable acids for use in the Friedlander condensation include the mineral acids, such as HCl, $H_2SO_4$, $HNO_3$ and $H_3PO_4$ as well as organic acids such as aromatic sulfonic acids and alkanoic acids having 1-10 carbon atoms, e.g., acetic acid. The most preferred organic acid is p-toluenesulfonic acid.

Suitable bases include inorganic bases such as carbonates, for example, sodium carbonate and potassium carbonate and organic bases such as tertiary $C_{1-12}$ amines, for example, trimethylamine, triethylamine, tripropylamine, etc., and bicyclic amines such as diazabicycloundecane (DBU). Alkoxides may also be used as the base with alkoxides having 1-6 carbon atoms being preferred. Preferred examples are methoxide, ethoxide, n-propoxide, isopropoxide, n-butoxide and t-butoxide.

In addition to the ortho-amino compounds noted above, the use of ortho-amino compounds having a hetero-atom incorporated in the aromatic ring is considered to be within the scope of the present invention. Preferred compounds have 5 or 6 membered aromatic rings and incorporate nitrogen, sulfur or oxygen in the ring. Camptothecin analogs containing a ring hetero atom are more fully described in U.S. application Ser. No. 07/032,449, filed Mar. 31, 1987 incorporated herein by reference.

The mother liquor remaining after isolation of the precipitated diastereomeric amide is enriched in the less polar amide and can be used to isolate this compound.

The mother liquor must first be concentrated to remove excess solvent. This concentration is typically carried out by application of a vacuum to remove the solvent. The product isolated after concentration contains predominantly the less polar amide although a minor proportion of the more polar amide generally remains. In order to obtain the optically pure camptothecin having the same configuration as the less polar amide, the amide must first be converted back to a lactone of the formula (I) and a second resolution step then performed. Conversion back to the lactone can be accomplished in a manner similar to that described above for the more polar amide, i.e., treatment with glacial acetic acid. The resulting lactone has the same configuration as the less polar diastereomeric amide from which it was produced.

Resolution of the enriched lactone mixture is accomplished in a manner similar to that disclosed above for the initial resolution reaction. However, the optically active amine should have the opposite configuration to the optically active amine used in the first resolution step. If for example R-α-methylbenzylamine is used in the initial resolution reaction, then S-α-methylbenzylamine should be used to resolve the enriched lactone mixture. If the original precipitated polar amide was of the R-configuration, then the enriched lactone mixture will be predominantly of the S-configuration. Reacting this enriched mixture with (S)-methylbenzylamine will then result in an enriched diastereomeric amide mixture containing the (R,S)-amide and the (S,S)-amide, enriched in the (S,S)-amide having formula (II).

Trituration of this enriched diastereomeric amide mixture with toluene will again precipitate the more polar amide, i.e., the (S,S)-amide in this case, leaving a mother liquor enriched in the (R,S)-amide. Subsequent acid treatment of the precipitated amide to effect lactonization and deprotection, followed by reaction of the resulting (S)-ketolactone (III) with an ortho-aminobenzaldehyde will yield the 20(S)-camptothecin or a 20(S)-camptothecin analog.

The treatment with a non-polar organic solvent, isolation of the precipitate, acid treatment and reaction with an ortho-amino compound can be performed in a similar manner to the reactions noted above for the initial resolution procedure.

Obviously, the particular optically active amine to be used is a matter of choice. Thus, for example, the process of the invention could be performed by first using an (S)-amine such as (S)-α-methylbenzylamine to isolate the (S,S)-amide and thereby obtain 20(S)-camptothecin, followed by the use of an (R)-amine, i.e., (R)-α-methylbenzylamine to isolate the (R,R)-amide and thereby obtain 20(R)-camptothecin.

The present method, therefore, enables the synthesis of optically pure 20(S)- and 20(R)-camptothecin and analogs thereof as pure optically active species by either of the methods noted above.

20(S)- and 20(R)-camptothecins and analogs thereof can be synthesized with an optical purity of greater than 50% by the method of the present invention. Higher optical purities such as, for example, 75-100% are also possible and are preferred. Most preferred are camptothecins and camptothecin analogs having an optical purity of 95-100%. The term "optical purity" is well known to those skilled in the art. A sample of 20(R)-camptothecin which is 50% optically pure will contain 75% 20(R)-camptothecin and 25% 20(S)-camptothecin.

Other features of the invention will become apparent in the course of the following descriptions of exemplary embodiments which are given for illustration of the invention and are not intended to be limiting thereof

EXAMPLES

Melting points were taken on a Kofler hot-stage microscope and are uncorrected. Infrared spectra were obtained on a Perkin-Elmer 267 spectrophotometer and $^1$H NMR spectra were determined on a Bruker 250 spectrometer at 250 MHz. Optical rotations were measured on a Rudolph Autopol III Automatic Polarimeter using a 1-cm$^3$ capacity quartz cell (10-cm path length). Elemental analyses were performed by Atlantic Microlab, Inc., Atlanta, Ga. Analytical HPLC analyses were performed on a Waters systems incorporating a Model 6000A pump, a Model 450 absorbance detector at 254 nm, and a Whatman Partisil 5 silica column (4.6 × 250 nm). The solvent system was 15% ethanol in hexanes at 2.0 mL/min. Radial preparative thick-layer chromatography was performed on a Harrison Chromatotron with a rotor coated to a 2-mm thickness (Merck silica gel 60, PF-254); column chromatography was carried out under medium pressure on a Merck Lobar Lichroprep Si 60 size B column. Preparative separation attempts employed 0.5-1.5% methanol in chloroform solvent mixtures.

R-(+)-α-methylbenzylamine and S-(−)-α-methylbenzylamine were purchased from Aldrich Chemical Company, Milwaukee, Wis.

Synthesis of the (R,R)-amide (II) and the (S,R)-amide (II)

A stirred suspension of the racemic lactone (I), wherein X is the —OCH$_2$CH$_2$O— group, (500 mg, 1.629 mol) in R-(+)-α-methylbenzylamine (3.0 mL) was heated under nitrogen to 70° C. whereupon a pale yellow solution resulted. Heating at 70° C. was maintained for 20 hr. and the excess amine was removed by high vacuum distillation to afford the crude mixture of the (R,R) and (S,R) diastereomers as an orange syrup. Partial separation of the (R,R) and (S,R) diastereomers (ca. 75% purities) on a 100 mg scale could be effected by radial thick layer chromatography or medium pressure silica column using 0.5-1.5% methanol in chloroform. The relative proportions of (R,R)-amide to (S,R)-amide were readily determined analytically by HPLC on Partisil 5 using 15% ethanol in hexane. The (R,R) isomer was the last to elute: (S,R)-amide, R$_t$ 10 min; (R,R)-amide, R$_t$ 11 min. A syrupy mixture of the (R,R)-amide and the (S,R)-amide obtained from (I) (500 mg) was dissolved in toluene (20 mL) and after 10 min the precipitated (R,R) isomer (215 mg) of 95% purity was removed by filtration. An optical purity of 100% was achieved by dissolving the sample in a minimum quantity of warm methylene chloride (0.5 mL) followed by dilution with toluene (5 mL). The pure (R,R) isomer crystallized as clear, colorless needles (138 mg); mp 121°-127° C.; IR (CHCl$_3$) 3410, 3540-3080 (NH, OH), 3000, 2980, 2900 (CH), 1658, 1650 (amide, pyridone), 1588 (aromatic), 1513, 1505, 1318, 1030 cm$^{-1}$; $^1$H NMR (CDCl$_3$) δ0.88 (t, 3H, J=7 Hz, —CH$_2$CH$_3$), 1.50 (d, 3H, J=7 Hz, Ar(N)CHCH$_3$), 2.03 (m, 1H, HCHCH$_3$), 2.18 (m, 1H, —HCHCH$_3$), 2.33 (t, 2H, J=7 Hz, —CH$_2$CH$_2$N—), 3.97 (t, 2H, J=7 Hz, —CH$_2$CH$_2$N), 4.12 (m, 4H, —OCH$_2$CH$_2$O—), 4.73 (d, 1H, J=13 Hz, ArHCHOH), 5.03 (d, 1H, J=13 Hz, ArHCHOH), 5.06 (m, 1H, Ar(N)CHCH$_3$), 5.93 (bs, 1H, 3' OH), 6.67 (s, 1H, pyridone H), 7.32 (m, 5H, aromatic), 7.48 (d, 1H, J=8 Hz, NH); $[\alpha]_D^{21}$ +56° (c 0.392, CHCl$_3$/MeOH, 4:1). Anal. Calcd. for C$_{23}$H$_{28}$N$_2$O$_6$.H$_2$O: C, 61.87; H, 6.77; N, 6.27. Found: C, 61.83; H, 6.76; N, 6.25.

5'(R)-1,5-Dioxo-(5'-ethyl-5'-hydroxy-2'H,5'H,6'H-6-oxopyrano([3', 4'-f] Δ$^{6,8}$-tetrahydroindolizine (I).

A solution of the (R,R)-amide (II) (33 mg, 0.0771 mmol) in glacial acetic acid (1 mL) was heated at 70° C. for 2 hr. and the solvent was removed in vacuo. The gummy product was dissolved in methylene chloride (5 mL) and the solution washed with water (1 mL). Drying (Na$_2$SO$_4$) and evaporation afforded the (R)-lactone (I) as a beige foam (23 mg) which crystallized as colorless short needles from ethyl acetate. The (R)-lactone was chromatographically identical to the authentic (RS)-lactone (I): mp 166°-167° C.; $[\alpha]_D^{21}$ −70° (conc. 0.333, CHCl$_3$/MeOH, 4:1)

The ketal group was cleaved by treatment of the (R)-lactone (23 mg, 0.0749 mmol) with dimethoxyethane (1 mL) and 2N aqueous sulfuric acid (0.4 mL) at 50° C. under nitrogen for 8 hr. The organic solvent was removed in vacuo, and the aqueous phase was extracted with chloroform (2×5 mL). The extract was dried (Na$_2$SO$_4$) and evaporated to yield the tricyclic (R)-ketolactone (III) (19 mg) as a pale foam. Recrystallization of the sample from ethyl acetate gave the (R)-ketolactone as near-colorless prisms having chromatographic and spectral properties identical to authentic racemic (III): mp 160°-170° C.; $[\alpha]_D^{21}$ −96° C. (c 0.3167, CHCl$_3$/MeOH, 4:1). (R)-ketolactone (III) can be obtained directly from the (R,R)-amide (II) by heating with sulfuric acid/dimethoxyethane.

The (R) configuration of ketolactone (III) was established by its reaction with o-aminobenzaldehyde using standard methods to give camptothecin of $[\alpha]_D^{21}$ −39°.

Synthesis of (R,S)-amide (II) and (S,S)-amide (II)

The toluene mother liquor from the isolation of the (R,R)-amide was concentrated in vacuo to give the crude (S,R)-amide containing about 20% of the (R,R)-amide as a yellow syrup (305 mg). The syrup was dissolved in glacial acetic acid (8 mL), and the stirred solution was heated under nitrogen at 70° C. for 7 hr. to regenerate lactone (I) enriched in the (S) isomer. The reaction mixture was evaporated under high vacuum to give a pale orange syrup which was partitioned between water (2 mL) and chloroform (10 mL). The organic phase was isolated, dried (Na$_2$SO$_4$) and evaporated to afford the (S)-lactone (I) contaminated with (R)-lactone (I) as an orange gummy foam (240 mg). The mixture was treated with S-(−)-α-methylbenzylamine (7 mL), and the stirred solution was heated at 75° C. for 20 hr. Excess amine was removed by high vacuum distillation to afford an orange-red syrup consisting of the (S,S)-amide contaminated with the (R,S)-amide. The sample was dissolved in toluene (5 mL) at room temperature, and within 10 min. nearly pure (S,S)-amide (II) had precipitated. The beige, powdery solid was dissolved in warm methylene chloride (0.5 mL) and diluted with toluene (5 mL). The clear, colorless needles which separated (110 mg) were composed of the (S,S)-amide with no evidence of contamination by the (R,S)-amide as determined by HPLC analysis (Partisil 5, 15% ethanol/hexanes). As expected, the enantiomeric pairs, i.e, the (R,R)-amide and (S,S)-amide were chromatographically and analytically identical except for $[\alpha]_D$ values; $[\alpha]^{21}$ for the (S,S)-amide −56° (conc. 0.392, CHCl$_3$/MeOH, 4:1) vs +56° C. obtained for the (R,R)-amide. Anal. of (S,S)-amide Calcd. for C$_{23}$H$_{28}$N$_2$O$_6$. H$_2$O; C, 61.87; H, 6.77; N, 6.27. Found: C, 61.74; H, 6.77; N, 6.24.

5'(S)-1,5-Dioxo-(5'-ethyl-5'-hydroxy-2'H,5'H, 6'H-6-oxopyrano)[3', 4'-f] Δ$^{6,8}$ -tetrahydroindolizine (S)-ketolactone (III)

A solution of the (S,S)-amide (36 mg, 0.0841 mmol) was treated with glacial acetic acid (1 mL) at 70° C. as described for the (R,R)-amide. The (S)-lactone (I) resulted as a beige foam (26 mg) which crystallized as rosettes of short colorless needles from ethyl acetate. The (S)-lactone (I) was analytically identical to the (R)-lactone (I) except for $[\alpha]_D^{21}$ which was determined to be +70° (conc. 0.250, CHCl$_3$/MeOH, 4:1).

As described for (R)-lactone (I) the ketal functionality in (S)-lactone (I) was hydrolyzed by heating in dimethoxyethane-2N sulfuric acid at 50° for 8 hr. Tricyclic (S)-ketolactone (III) was isolated as a pale tan foam (20 mg) which was recrystallized from ethyl acetate to give the pure product as colorless prisms. Except for $[\alpha]_D^{21}$ +96° (conc. 0.4, CHCl$_3$/MeOH, 4:1), (S)-ketolactone was identical to the (R)-ketolactone, and differed from authentic racemic ketolactone with respect to mp 169°-170° C. vs 185°-187° C. As described for (R)-ketolactone, the (S)-ketolactone can be obtained directly from the (S,S)-amide (II) using strongly acidic conditions.

The S configuration of ketolactone (III) was confirmed by the generation of 20(S)-camptothecin of $[\alpha]_D^{21}$ +39° from the condensation of (S)-ketolactone with o-aminobenzaldehyde.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for producing substantially pure 20(S)-camptothecin, 20(R)-camptothecin or analogs thereof, comprising the steps of:

(a) reacting a mixture of enantiomeric lactones having formula (I), wherein X is an achiral ketal group which upon treatment with an acid is converted into a keto group,

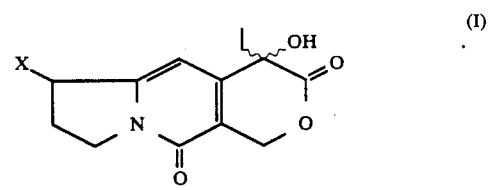

with a substantially enantiomerically pure primary or secondary amine having the formula RR$^1$NH, wherein R is an alkyl or aralkyl group containing a single chiral carbon and R$^1$ is hydrogen or an achiral alkyl, aralkyl or aryl group, to produce a mixture of diastereomeric amides with formula (II)

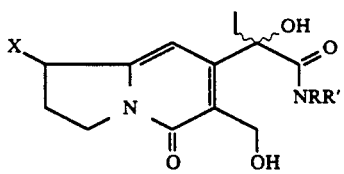

(II)

(b) triturating said diastereomeric amide mixture with a non-polar organic solvent whereby a precipitate enriched in the more polar amide of said diastereomeric mixture and a mother liquor enriched in the less polar amide of said diastereomeric amide mixture are formed;

(c) separating said precipitate from said mother liquor;

(d) treating said precipitated amide with acid, whereby said precipitated amide is lactonized and deprotected to give an enantiomerically enriched ketolactone having formula (III)

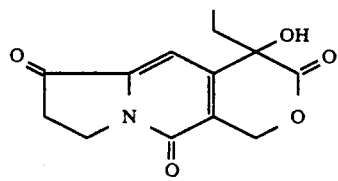

(III)

(e) reacting said ketolactone with an ortho-amino carbonyl compound having the formula

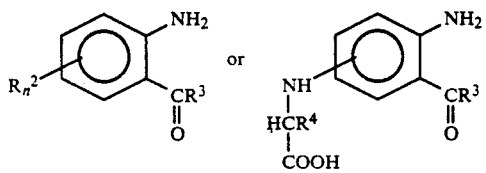

wherein n=1 or 2 and $R^2$ is a member selected from the group consisting of $C_{1-8}$ alkyl, $C_{1-8}$ alkoxy, cyano, methylenedioxy, formyl, hydroxy, nitro, amino, amido, chloro, bromo, iodo, fluoro, aminomethyl, trifluoromethyl, azido, and hydrazinyl groups, $R^3$ is H or $C_{1-8}$ alkyl; and $R^4$ is a side-chain of one of the twenty naturally occurring amino acids, to produce said camptothecin or camptothecin analog; and (f) isolating said camptothecin or camptothecin analog.

2. The method of claim 1, wherein said amine is selected from the group consisting of R and S enantiomers of α-methylbenzylamine, α-(1-naphthyl)-ethylamine, α-(2-naphthyl)-ethylamine and amphetamine.

3. The method of claim 2, wherein said amine is R-α-methylbenzylamine or S-α-methylbenzylamine.

4. The method of claim 1, wherein said nonpolar organic solvent is selected from the group consisting of aliphatic, aromatic and araliphatic hydrocarbons having 6-20 carbon atoms.

5. The method of claim 4, wherein said nonpolar organic solvent is toluene.

6. The method of claim 1, wherein said acid is a mineral acid or an organic acid.

7. The method of claim 6, wherein said acid is aqueous sulfuric acid.

8. The method of claim 1, wherein said treating step comprises
lactonizing said precipitated amide in the presence of glacial acetic acid, and
deprotecting said lactone in the presence of aqueous sulfuric acid.

9. The method of claim 1, further comprising:

(g) concentrating said mother liquor to produce a product enriched in said less polar amide and treating said enriched product with an acid to give an enriched mixture of lactones having formula (I);

(h) reacting said enriched mixture of lactones with a second substantially enantiomerically pure amine, wherein said second amine has a configuration opposite that of the amine used in step (a), to give an enriched mixture of diastereomeric amides having formula (II);

(i) turating said enriched mixture of diastereomeric amides with a non-polar organic solvent, whereby the more polar amide of said enriched mixture precipitates;

(j) separating said enriched precipitate from said nonpolar organic solvent;

(k) treating said precipitate with an acid, whereby said precipitate is lactonized and deprotected to give a substantially enantiomerically pure ketolactone having formula (III);

(l) reacting said ketone with an ortho-amino carbonyl compound having the formula

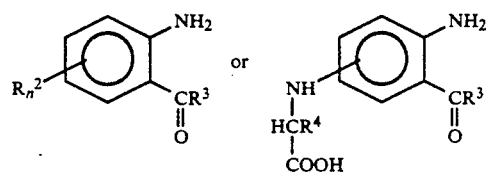

wherein n=1 or 2 and $R^2$ is a member selected from the group consisting of $C_{1-8}$ alkyl, $C_{1-8}$ alkoxy, cyano, methylenedioxy, formyl, hydroxy, nitro, amino, amido, chloro, bromo, iodo, fluoro aminomethyl, trimethylamino, azido, and hydrazinyl groups; $R^3$ is H or $C_{1-8}$ alkyl; and $R^4$ is a side-chain of one of the twenty naturally occurring amino acids; and (m) isolating said camptothecin or camptothecin analog.

10. The substantially pure 20(S)-camptothecin which is 10,11-methylenediox-20(S)-camptothecin.

11. The 20(S)-camptothecin of claim 10, having an optical purity of 75-100%.

12. The 20(S)-camptothecin of claim 11, having an optical purity of 95-100%.

* * * * *